United States Patent [19]
Nakabayashi et al.

[11] Patent Number: 5,554,669
[45] Date of Patent: Sep. 10, 1996

[54] EMULSION OF POLYMER HAVING (METH)ACRYLATE UNIT AND ADHESIVE COMPOSITIONS CONTAINING THE EMULSION

[75] Inventors: Nobuo Nakabayashi, 5-6-20 Koganehara, Matsudo-shi, Chiba-ken; Kazuhiko Ishihara, Kodaira; Yasukazu Saimi, Moriyama, all of Japan

[73] Assignees: Mitsui Petrochemical Industries, Ltd., Tokyo; Nobuo Nakabayashi, Matsudo, both of Japan

[21] Appl. No.: 327,414

[22] Filed: Oct. 21, 1994

Related U.S. Application Data

[63] Continuation-in-part of Ser. No. 066,211, May 25, 1993, abandoned.

[30] Foreign Application Priority Data

May 27, 1992 [JP] Japan ................................. 4-158945

[51] Int. Cl.$^6$ ............................ C08L 33/08; C08L 33/10
[52] U.S. Cl. ........................ 523/118; 523/116; 525/309
[58] Field of Search .................................. 523/116, 118, 523/111; 525/274, 309

[56] References Cited

U.S. PATENT DOCUMENTS

| | | |
|---|---|---|
| 4,791,162 | 12/1988 | Vanderhoff et al. . |
| 4,916,191 | 4/1990 | Takeuchi et al. . |
| 5,243,006 | 9/1993 | Nakabayashi ............................ 523/118 |
| 5,338,773 | 8/1994 | Lu ............................................ 523/116 |

OTHER PUBLICATIONS

Patent Abstracts of Japan vol. 15, No. 12 (C–0795)10 Jan. 1991 & JP–A–22 61 442 (Mitsui Petrochem. Ind. Ltd.) 24 Oct. 1990.

Chemical Abstracts, vol. 98, No. 20, 16 May, 1983, Columbus, Ohio US; abstract No. 161233s, & Kobunshi Ronbunshu vol. 40, No. 2, pp. 93–99 Okubo, et al.: 'Studies on suspension and emulsion . . . '.

Chemical Abstract, vol. 88, No. 14 Columbus, Ohio, US; abstract No. 90443r, & JP–A–52 117 390 (Japan Exlan Co., Ltd.) 1 Oct. 1977.

Database WPI Week 9116, Derwent Publications Ltd., London, GB; AN 91-112723 & JP–A–3 052 981 (Saiden Kagaku K. K.) Mar. 1991.

Chemical Abstracts, vol. 97, No. 10, 6 Sept. 1982, Columbus, Ohio, US; abstract No. 7287t, & Nippon Setchaku Kyokaishi vol. 18, No. 4, pp. 153–158, Okubo, et al.: 'Studies on suspension and emulsion . . . '.

Chemical Abstracts, vol. 116, No. 18, 4 May 1992, Columbus, Ohio, US; abstract No. 181077n, & Kobunshi Ronbunshu vol. 49, No. 2, pp. 119–123 Yamamoto, et al.: 'Synthesis and adhesion of graft polymer. . . '.

Chemical Abstracts, vol. 111, No. 8 Columbus Ohio US; abstract No. 58884t, & JP–A–63 289 051 (Japan Exlan Co., Ltd.) 25 Nov. 1988.

Chemical Abstracts, vol. 97, No. 2, Columbus, Ohio, US; abstract No. 6983X. & JP–A–57 030 703 (Toyo Soda Mfg. Co., Ltd.) 19 Feb. 1982.

Chemical Abstracts, vol. 111, No. 18 Columbus, Ohio, US: abstract No. 154575p, & JP–A–63 270 535 (Kyowa Gas Chemical Industry Co., Ltd.) 8, Nov. 1988.

*Primary Examiner*—Christopher Henderson
*Attorney, Agent, or Firm*—Sherman & Shalloway

[57] ABSTRACT

An emulsion of a polymer, in which the polymer comprises (a) a recurring unit derived from a (meth)acrylate and (b) a recurring unit derived from a vinyl compound having a group of —$SO_3R$ in which R is a hydrogen atom, an alkali metal atom or ammonium ion. The emulsion forms a film on an adherend to decrease the infiltration into the adherend, exhibits an adhesion force to a hydroxyapatite structure, a cement, a metal or a mineral when it is applied thereto to form a film by only drying around room temperature without washing it with water, and exhibits excellent affinity to a radical-polymerizable acrylic resin composition.

17 Claims, No Drawings

5,554,669

EMULSION OF POLYMER HAVING (METH)ACRYLATE UNIT AND ADHESIVE COMPOSITIONS CONTAINING THE EMULSION

This is a continuation-in-part application based on U.S. patent application Ser. No. 08/066,211 filed on May 25, 1993, now abandoned.

BACKGROUND OF THE INVENTION

The present invention relates to an emulsion of a polymer having a (meth)acrylate unit and adhesive compositions containing the emulsion. More specifically, it relates to a polymer emulsion which reacts to be fixed on the surface of a solid containing a polyvalent cation reactive with a sulfonic acid group, such as a hydroxyapatite structure, cement, a metal compound or a mineral, an adhesive film from the polymer emulsion formed on the surface of said solid and an adhesive composition which exhibits excellent adhesion to a substrate.

The above adhesive film exhibits excellent adhesion to a tooth and excellent sealability to dental tubules, so that it can be suitably used as a dental primer and a dental antihypersensitivity film.

For treating a hydroxyapatite structure such as a dentin for remedy, an adhesive material such as 4-META/MMA-TBB (Superbond, supplied by Sun Medical Co., Ltd) has been hitherto used. The adhesive material is bonded by a method in which a drilling dust is removed by preliminary etching of an adherend surface with an acid, the adhesive material is applied and cured and then a radical-polymerizable acrylic resin is filled and cured. Since, however, the acid used for the above acid treatment is a low molecular weight compound, it may infiltrate deep into the hydroxyapatite structure. Therefore, when a dentin is treated for remedy, the acid comes to remove a healthy part of the dentin as well and sometimes reaches a dental pulp to attack the nerve and give an acute pain.

Therefore, when a portion near to a dental pulp is treated for remedy, there has been conventionally employed a method in which the attack in bonding is prevented by applying onto the above portion a carboxylate cement which is a combination of a polymer type polyaerylle acid with zinc oxide or a glass ionomer cement which is a combination of a homopolymer of polyacrylic acid or a copolymer from acrylic acid and either itaconic acid or maleic acid with aluminosilicate glass.

Since, however, these cements are very poor in adhesion, there have been problems such as secondary caries and coming off of the attachment for remedy.

For the therapeutical treatment of the hypersensitivity of a dentin based on exposure of dental tubules in the mouth, there are used a liniment of silver nitrate, potassium oxalate or disodium hydrogenphosphate/calcium chloride (Ikemura, Imal, Journal of Japanese Dentistry Preservation Society, vol. 35, 26 (1992)), a toothpaste containing citric acid or sodium citrate, a glass ionomer cement and a 4-META-containing adhesive resin (D liner, supplied by Sun Medical Co., Ltd).

The above preparations against the hypersensitivity of a dentin have the following advantages. The liniment is free of stimulation to a dental pulp and coloring, and the toothpaste obviates the therapeutical treatment in a dentist's chair. However, it is usual that it takes a long period of time before they exhibit their effects. The polymer type carboxylic acid such as glass ionomer hardly affects a dentin. However, it is poor in adhesion to a dentin and resistance to water, and its effect does not continue satisfactorily. On the other hand, the adhesive resin shows its effect, but is used for the therapy by a method in which a portion to be treated is preliminarily etched with a low molecular weight acid such as a 10% citric acid–3% ferric chloride aqueous solution or the like, and a solution prepared by mixing a curing agent and a monomer immediately before use is applied and polymerized. Therefore, it still involves a problem in the influence of the low molecular weight compound on a dentin and handling.

Further, VARNAL® (CETYLITE INDUSTRIES INC. (U.S.A.)) is commercially available, which is used for alleviating the cervical hyperesthesis by applying it in the form of a solution to the dental surface of cervical hyperesthesis and drying it to form a film. This method of treating a tooth surface is similar to that employed in the present invention. However, VARNAL is a solution prepared by dissolving a copal resin which is a natural resin in an alcohol solvent, and is basically different from the present invention in the following points: VARNAL does not contain any sulfonic acid group which is an essential component for the emulsion of an emulsion-polymerizable polymer of the invention, it may not be facile to acquire the copal resin since it is a natural resin and difficult to synthesize, and VARNAL is poor in adhesion to a tooth.

For decreasing the infiltration of an acid into a hydroxyapatite structure and imparting it with affinity to an acrylic resin, the present Applicant has proposed an acrylate copolymer containing a sulfonic acid group which allows to ion-bond or chelate-bond to a calcium component of the hydroxyapatite structure (Japanese Laid-open Patent Publications Nos. 171,024/1985 and 261,442/1990).

The polymer disclosed in the above Japanese Laid-open Patent Publications is specifically an acrylic copolymer produced from methacrylate such as methyl methacrylate and a sulfonic acid group-containing monomer such as p-styrenesulfonic acid and/or methacrylate macromet having a vinyl group at its terminal such as methyl polymethacrylate. These Publications disclose a method in which the above acrylic copolymer is dissolved in a solvent such as water or ethanol, the resultant solution is applied directly to a hydroxyapatite structure surface without acid etching and the resultant coating is washed with water. In this method, the degree of infiltration into the hydroxyapatite structure is small, the copolymer firmly bonds to the hydroxyapatite structure since the sulfonic acid group bonds to a calcium component of the hydroxyapatite structure, and the hydroxyapatite structure can be bonded to an acrylic resin to form a layer thereon since the polymethyl methacrylate portion of the acrylic copolymer and the acrylic resin have good affinity.

However, further studies of the above acrylic copolymer have revealed the following. When a solution of the acrylic copolymer is applied and dried without washing it with water, the acrylic copolymer sometimes shows no adhesion force due to a presence of a remaining unreacted acrylic copolymer which does not react with the hydroxyapatite structure. It is therefore essential to carry out a step of washing with water for obtaining a stable adhesion force.

It is an object of the present invention to provide a novel adhesive emulsion to overcome the above problems and an adhesive composition containing the same.

It is another object of the present invention to provide a novel adhesive emulsion which decreases the infiltration into an adhererid, like a conventional sulfonic acid group-containing copolymer, which exhibits an adhesion force to a hydroxyapatite structure, a cement, a metal or a mineral when it is applied thereto and, without washing it with water, only dried around room temperature to form a film, which exhibits excellent affinity to a radical-polymerizable acrylic resin composition, and which further permits sealing the surface of a hypersensitive dentin since a film formed therefrom has the property of bonding to a dentin which is a hydroxyapatite structure.

Other objects and advantages of the present invention will be apparent from the following description.

SUMMARY OF THE INVENTION

According to the present invention, the above objects and advantages of the present invention are achieved, first, by an emulsion of a polymer, in which the polymer comprises (a) a recurring unit derived from a (meth)acrylate and (b) a recurring unit derived from a vinyl compound having a group of —$SO_3R$ in which R is a hydrogen atom, an alkali metal atom or ammonium ion and is derived from a mixture containing the (meth)acrylate and the vinyl compound having a group of —$SO_3R$ in which R is as dellned above in a (meth)acrylate:vinyl compound molar ratio of 99:1 to 50:50 by a soap-free emulsion polymerization.

The polymer emulsion according to the present invention may be an emulsion of a polymer which further contains (c) a recurring unit derived from a vinyl compound containing a group of —$COOR_4$ in which $R_4$ is a hydrogen atom, an alkali metal atom or ammonium ion, or a group of —$OPO(OR_5)_2$ in which $R_5$ is a hydrogen atom, an alkali metal atom or ammonium ion and is derived from a mixture containing the (meth)acrylate, the vinyl compound having a group of —$SO_3R$ in which R is as defined above, and the vinyl compound containing a group of —$COOR_4$ or a group of —$OPO(OR_5)_2$ in which $R_4$ and $R_5$ are as defined above in the molar ratio of (meth)acrylate:total of the two vinyl compounds of 99:1 to 50:50 and in the molar ratio of the vinyl compound having a group of —$SO_3R$ in which R is as defined above to the vinyl compound containing a group of —$COOR_4$ or a group of —$OPO(OR_5)_2$ in which $R_4$ and $R_5$ are as defined above of 99:1 to 1:99.

The above (a) recurring unit derived from (meth)acrylate has the formula (A) for example,

wherein $R_1$ is a hydrogen atom or an alkyl group having 1 to 5 carbon atoms and $R_2$ is an alkyl group having 1 to 5-carbon atoms.

The above (b) recurring unit derived from a vinyl compound having a group of —$SO_3R$ has the formula (B),

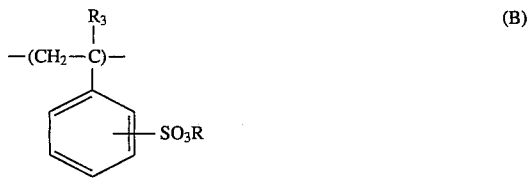

wherein $R_3$ is a hydrogen atom or an alkyl group having 1 to 5 carbon atoms and R is a hydrogen atom, an alkali metal atom or ammonium ion.

Further, according to the present invention, there is provided a polymer emulsion obtained by emulsion-polymerizing (meth)acrylate in the presence of the above emulsion polymer as an emulsifying agent.

Still further, according to the present invention, there is provided the following polymer emulsions: (1) a polymer emulsion obtained by emulsion-polymerizing (meth)acrylate in the presence of an emulsion of a polymer as an emulsifying agent, said polymer of the latter emulsion as tile emulsifying agent being obtained by emulsion-polmerizing (a) a (meth)acrylate and (b1) a vinyl compound having a group of —$SO_3R$ in which R is a hydrogen atom in the absence of a soap in an (a):(b1) molar ratio of 99:1 to 50:50.

(2) a polymer emulsion obtained by emulsion-polymerizing (meth)acrylate in the presence of an emulsion of a polymer as an emulsifying agent, said polymer of the latter emulsion as the emulsifying agent being obtained by emulsion-polymerizing (a) a (meth)acrylate and (b1) a vinyl compound having a group of —$SO_3R$ in which R is an alkali metal atom or ammonium ion in the absence of a soap in an (a):(b1) molar ratio of 99:1 to 50:50, and thereafter converting said group of —$SO_3R$ to —$SO_3H$ group.

(3) a polymer emulsion obtained by emulsion-polymerizing (meth)acrylate in the presence of an emulsion of a polymer as an emulsifying agent, said polymer of the latter emulsion as the emulsifying agent being obtained by emulsion-polymerizing (a) a (meth)acrylate, (b1) a vinyl compound having a group of —$SO_3R$ in which R is a hydrogen atom and (c1) a vinyl compound containing a group of —$COOR_4$ in which $R_4$ is a hydrogen atom, or a group of —$OPO(OR_5)_2$ in which $R_5$ is a hydrogen atom, in the absence of a soap in the molar ratio of (meth)acrylate (a):total of the two vinyl compounds (b1) and (c1) of 99:1 to 50:50 and in the molar ratio of the vinyl compound (b1):the vinyl compound (c1) of 99:1 to 1:99.

(4) a polymer emulsion obtained by emulsion-polymerizing (meth)acrylate in the presence of an emulsion of a polymer as an emulsifying agent, said polymer of the latter emulsion as the emulsifying agent being obtained by emulsion-polymerizing (a) a (meth)acrylate, (b1) a vinyl compound having a group of —$SO_3R$ in which R is an alkali metal atom or ammonium ion and (c1) a vinyl compound containing a group of —$COOR_4$ in which $R_4$ is an alkali metal atom or ammonium ion, or a group of —$OPO(OR_5)_2$ in which $R_5$ is an alkali metal atom or ammonium ion, in the absence of a soap in the molar ratio of (meth)acrylate (a):total of the two vinyl compounds (b1) and (c1) of 99:1 to 50:50 and in the molar ratio of the vinyl compound (b1):the vinyl compound (c1) of 99:1 to 1:99, and thereafter converting said groups of —$SO_3R$, —$COOR_4$ and —$OPO(OR_5)_2$ to —$SO_3H$, —$COOH$ and —$OPO(OH)_2$, respectively.

The recurring unit derived from the (meth)acrylate preferably has the above formula (A) and the recurring unit derived from the vinyl compound having a group of —$SO_3H$ has the above formula (B) wherein R is a hydrogen atom.

DESCRIPTION OF THE PREFERRED EMBODIMENTS

The polymer emulsion according to the present invention is produced, for example, by emulsion-polymerizing a (meth)acrylate of the formula (A1),

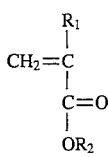

(A1)

wherein $R_1$ and $R_2$ are as defined in the above formula (A),
with a sulfonic acid group-containing monomer of the formula (B1),

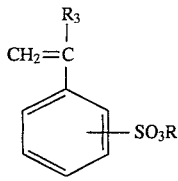

(B1)

wherein $R_3$ and R are as defined in the above formula (B), preferably in an (A1): (B1) molar ratio of 99: 1 to 50:50 or by homopolymerizing one (meth)acrylate monomer of the formula (A1), or copolymerizing (meth)acrylate monomers of the formula (A1), in the presence of the so-obtained emulsion polymer as an emulsifying agent.

Further, in the production of the polymer emulsion according to the present invention, the polymer emulsion is produced by emulsion-polymerizing the vinyl compounds of the above formulae (A1) and (B1) and either (E) a vinyl compound having a group of —$COOR_4$ or (F) a vinyl compound having a group of —$OPO(OR_5)_2$ in which $R_4$ and $R_5$ are as defined above, preferably in an (A1):(B1)+(E) or (A1):(B1)+(F) molar ratio of 99:1 to 50:50 and in a (B1):(E) or (B1):(F) molar ratio of 99:1 to 1:99, or by homopolymerizing one (meth)acrylate monomer of the formula (A1), or copolymerizing (meth)acrylate monomers of the formula (A1), in the presence of the so-obtained emulsion polymer as an emulsifying agent.

Being constituted by the specific recurring units, the emulsion polymer obtained in the present invention can form a film having the excellent property of bonding to a sulfonic acid group of a hydroxyapatite structure, a cement, a metal compound or a mineral. Therefore, a dentin such as a hypersensitive dentin surface can be sealed with an adhesive film. Further, since it shows excellent affinity to a radical-polymerizable acrylic resin, it can be properly used as an adhesive for bonding a dentin and a radical-polymerizable acrylic resin.

The adhesive emulsion, process for the production thereof and adhesive composition containing the same, provided by the present invention, will be explained hereinafter.

First, the process for the production of the adhesive emulsion will be explained. In the present invention, the term "emulsion polymer" refers to a polymer obtained by emulsion polymerization, and the term "polymer emulsion" refers to an emulsion of the emulsion polymer.

The polymer emulsion (to be referred to as "EM" hereinafter) in the present invention can be produced by subjecting a (meth)acrylate of the above formula (A1) and a vinyl compound having a group of —$SO_3R$ in which R is a hydrogen atom, an alkali metal atom or ammonium ion, represented by the above formula (B1), to a known emulsion polymerization method (e.g., "Polymer Latex", Soichi Murol, Ikuo Morino, published as Shin-Kobunshi Bunko).

In the formula (A1), $R_1$ is a hydrogen atom or an alkyl group having 1 to 5 carbon atoms. Specific examples of the alkyl group include methyl, ethyl, propyl, butyl and pentyl. $R_1$ is preferably an alkyl group having 1 to 5 carbon atoms, more preferably methyl.

Further, $R_2$ is an alkyl group having 1 to 5 carbon atoms. Specific examples of the alkyl group include methyl, ethyl, propyl, butyl and pentyl. $R_2$ is preferably methyl, ethyl or butyl, more preferably methyl.

Examples of the compound of the above formula (A1) preferably include (meth)acrylates such as methyl (meth)acrylate, ethyl (meth)acrylate, butyl (meth)acrylate, propyl (meth)acrylate, pentyl (meth)acrylate, glycidyl (meth)acrylate, 2-hydroxy (meth)acrylate and 3-hydroxy (meth)acrylate.

Of the above (meth)acrylates, preferred are methyl methacrylate, ethyl methacrylate and butyl methacrylate, and particularly preferred is methyl methacrylate.

In the present invention, there is used another monomer having a group of —$SO_3R$ in which R is a hydrogen atom, an alkali metal atom or ammonium ion. Specifically, the monomer includes vinyl compounds or alkyl group-substituted vinyl compounds to which the group of —$SO_3R$ in which R is as defined above bonds directly or through other group.

Examples of the above sulfonic acid group-containing monomer preferably include allylsulfonic acid, methallylsulfonic acid, vinylsulfonic acid, o-styrenesulfonic acid, m-styrenesulfonic acid, p-styrenesulfonic acid, tert-butylacrylamidesulfonic acid, alkali metals salts of these acids such as lithium salts, potassium salts and sodium salts, and ammonium salts of the above acids. Of these, preferred are compounds in which the above group of —$SO_3R$ bonds to a carbon atom which is part of a polymerizable group, such as styrenesulfonic acids. These compounds are preferably represented by the above formula (B1).

In the above formula (B1), $R_3$ is a hydrogen atom or an alkyl group having 1 to 5 carbon atoms. The alkyl group includes methyl, ethyl, propyl, butyl and pentyl. $R_3$ is preferably a hydrogen atom.

The position at which the group of —$SO_3R$ bonds may be any one of the o-position, m-position and p-position in the benzene ring. In view of the adhesion to an adherend, preferred is the p-position. Further, the group of —$SO_3R$ may be any one of a lithium salt, potassium salt, sodium salt and ammonium salt. Examples of the compound of the above formula (B1) preferably include sulfonic acid compounds such as allylsulfonic acid, methallylsulfonic acid, vinylsulfonic acid, sulfoethyl methacrylate, tert-butylacrylamidesulfonic acid and p-styrenesulfonic acid, and sodium salts and ammonium salts of these. Of these examples, preferred is p-styrenesulfonic acid.

Examples of the above (E) monomer having a group of —$COOR_4$ in which $R_4$ is a hydrogen atom, an alkali metal atom or ammonium ion include unsaturated monovalent carboxylic acids such as acrylic acid, methacrylic acid, vinylacetic acid, crotonic acid, methacryloyloxybenzoic acid, vinylsalicylic acid and vinylacetylsalicyclic acid; alkali metal salts of these acids; ammonium salt compounds of these acids; unsaturated polyvalent carboxylic acids such as maleic acid, fumaric acid, itaconic acid, aconitic acid, citraconic acid, mesaconic acid and 4-methacryloyloxyethyltrimellitic acid; alkali metal salts of these acids; and ammonium acid compounds of these acids. Of these, preferred are acrylic acid and methacrylic acid.

Examples of the above (F) monomer having a group of —$OPO(OR_5)_2$ in which $R_5$ is a hydrogen atom, an alkali metal atom or ammonium ion include phosphate ester monomers such as acid phosphoethyl (meth)acrylate, 3-chloro-2-acid phosphopropyl (meth)acrylate, acid phosphooxypropyl (meth)acrylate, acid phosphooxypolyoxyethylethylene glycol mono(meth)acrylate and acid phosphooxypolyoxypropylene glycol mono(meth)acrylate; alkali metal salts of these; ammonium salt-containing monomers of these; and those compounds derived from the above compounds in which the hydroxyl group is substituted with other substituent, i.e., phosphate ester type monomers such as 2-(meth) acryloyloxyethylphenyl phosphate and 2-(meth)acryloyloxyethyl 4-methoxyphenyl phosphate. Of these, acid phosphooxyethyl methacrylate or acid phosphooxyethylene glycol monomethacrylate is useful.

In the emulsion polymerization in the present invention, the molar ratio of the monomor of the above formula (A1) to the monomer of the above formula (B1) is preferably as shown below, since an excellent emulsion can be obtained and since the acidity decreases to prevent the infiltration into an adherend. That is, the molar ratio of the monomer of the formula (A1) and the monomer of the formula (B1) is preferably 99:1 to 50:50, more preferably 95:5 to 60:40. Further, concerning the molar ratio of the monomer of the formula (A1) and the monomer of the formula (B1) and either the (E) vinyl compound having a group of —$COOR_4$ or the (F) vinyl compound having a group of —$OPO(OR_5)_2$ in which $R_4$ and $R_5$ are as defined above, preferably, the (A1):(B1)+(E) or (B1)+(F) molar ratio is 99:1 to 50:50 and that the (B1):(E) or (F) molar ratio is 99:1 to 1:99, and more preferably, the (A1):(B1)+(E) or (B1)+(F) molar ratio is 95:5 to 60:40 and that the (B1):(E) or (F) molar ratio is 99:1 to 5:95.

The reaction conditions for the emulsion polymerization are not specially limited. For example, an excellent polymer emulsion can be produced, for example, by adding a mixture of (A1) and (B1) or (A1), (B1) and optionally either (E) or (F) to water in an amount of 60 parts by weight or less per 100 parts by weight of the water at a temperature ranging from room temperature to 100° C., addling an initiator for emulsion polymerization and polymerizing them for tens minutes to 24 hours. When the monomer mixture is added at one time, an emulsion containing a large amount of aggregates is liable to be formed. It is therefore preferred to add the monomer mixture Intermittently.

The emulsion polymerization may be carried out in the presence or absence of a surfactant such as an anionic surfactant, a cationic surfactant, a nonionic surfactant or a polymer surfactant such as polyethylene glycol. In the absence of a surfactant, however, there can be produced a polymer emulsion which is free of aggregates, has high stability in water and has an emulsion particle diameter of 1 μm or less. For simple post-treatment and for avoiding the impairment of the adhesion and film strength of the polymer emulsion, it is preferred to carry out soap-free emulsion polymerization in the absence of a surfactant. Further, when the above monomer (E) or (F) is used, it is preferred to produce the emulsion under an acidic condition of pH 6 or less for maintaining the emulsion stability in a good state.

In addition to the above monomers, other monomer which is generally emulsion-polymerizable may be copolymerized in such an amount that does not impair the properties of the adhesive composition of the present invention. Examples of the "other monomer" include glycidyl esters such as N-(2-hydroxy-3-methacryloyloxypropyl)-N-phenylglycine, glycidyl (meth)acrylate and N-acrylglycine; (meth)acrylates having an alkylamino group such as N,N-dimethylaminoethyl (meth)acrylate, aminoethyl (meth)acrylate and hydroxyethylaminoethyl (meth)acrylate; olefins such as ethylene, propylene and 1-butene; vinyl halides such as vinyl chloride, vinylidene chloride, vinyl bromide, 2-chloroethyl (meth)acrylate, 1,1-dichloroethylene and tetrachloroethylene; vinyl esters such as vinyl acetate and vinyl propionate; (meth)acrylaldehydes such as (meth)acrylaldehyde and 3-cyano(meth)acrylaldehyde; vinyl ethers such as methyl vinyl ether, isobutyl vinyl ether, (meth)acrylaldehyde diacetate, (meth)acrylaldehyde diethyl acetal and 1,2-dimethoxyethylene; alkenylbenzenes such as styrene, vinyltoluene, α-methylstyrene, chloromethylstyrene, stilbene and 1,1-diphenylethylene; vinyl cyanide compounds such as acrylonitrile and methacrylonitrile; (meth)acrylamides such as (meth)acrylamide, N-vinylphthalamide, N-vinylsuccinamide, N,N-dimethylacrylamide, N-hydroxymethyl-(meth)acrylamide and N-hydroxyethyl-2-methylacrylamide; and (meth)acrylates having a hydroxyl group such as hydroxylmethyl (meth)acrylate, 2-hydroxyethyl (meth)acrylate and 4-hydroxybutyl (meth)acrylate.

The process for the production of an emulsion polymer by homopolymerizing or copolymerizing (meth)acrylate(s) (A1) in the presence of the above-obtained polymer emulsion (EM) as an emulsifying agent will be explained hereinafter.

The (meth)acrylate(s) used in the above process are the compound(s) of the formula (A1).

In this process, specific examples of the alkyl group as $R_1$ and $R_2$ in the formula (A1) also include methyl, ethyl, propyl, butyl and pentyl. $R_1$ is preferably an alkyl group, more preferably methyl. $R_2$ is preferably methyl.

In this process, preferred examples of the compound of the formula (A1) include alkyl esters of (meth)acrylic acids such as methyl (meth)acrylate, ethyl (meth)acrylate, butyl (meth)acrylate, propyl (meth)acrylate, pentyl (meth)acrylate and glycidyl (meth)acrylate.

Of the above (meth)acrylates, methyl methacrylate is particularly preferred.

The method of emulsion-polymerization of the (meth)acrylate of the formula (A1) has a characteristic feature in that the above-detailed polymer emulsion "EM" is used as an emulsifying agent.

The above polymer emulsion "EM" may be added to the (meth)acrylate compound of the formula (A1) as an emulsifying agent after it has been taken out of a reaction vessel. Further, the above polymer emulsion "EM" may be used in a manner in which the (meth)acrylate compound of the formula (A1) is added to it while it is in a reaction vessel, i.e., without being taken out of a reaction vessel, after it has been produced.

The reaction conditions are not specially limited, while, for example, the polymer emulsion can be produced by adding the (meth)acrylate compound of the formula (A1) to the polymer emulsion "EM" within the temperature range between room temperature and 100° C. after the polymer emulsion has been produced, and emulsion-polymerizing the resultant mixture for tens minutes to 24 hours.

The mixing ratio of the polymer emulsion "EM" and the monomer of the formula (A1) and the amounts of these based on water are not specially limited. Preferably, the "EM": (A1) weight ratio is 1:99 to 80:20, and the total amount of "EM" and the monomer (A1) per 100 parts by weight of water is 60 parts by weight or less.

The type of the emulsion polymer and the composition of the copolymer can be varied by intermittently changing the kind of the (meth)acrylate compound (A1) and the composition of the mixture in the polymerization system.

For forming an adhesive film having higher adhesion strength by applying the polymer emulsion of the present invention to a hydroxyapatite structure, preferably, a tooth and the surface of cervical hyperesthesia, all of —$SO_3R$, —$CO_2R_4$ and —$OPO(OR_5)_2$ as components forming the emulsion are substantially acid types, 1.e., —$SP_3H$, —$CP_2H$ and —OPO(OH)$_2$. That is because the adhesion strength increases as the proportion of acid types in acid groups increases.

For the above purpose, it is preferred to employ a method in which, after the production of "EM", the above R, R$_4$ and R$_5$ (each of R, R$_4$ and R$_5$ is an alkali metal atom or ammonium ion) are replaced with hydrogen atoms using mineral acids such as hydrochloric acid and sulfuric acid or an ion-exchange resin and then (A1) is emulsion-polymerized or a method in which (A1) is emulsion-polymerized in the presence of "EM" as an emulsifier and then —SO$_3$R, —CO$_2$R$_4$ and —OPO(OR$_5$)$_2$ (each of R, R$_4$ and R$_5$ is an alkali metal atom or ammonium ion) are converted to acid types by the above method.

Further, after the emulsion polymer is converted to an acid type, it is preferred to remove compounds having low molecular weights such as sodium chloride and sodium sulfate by a dialysis method or an ultrafiltration method, if they are formed.

In the above polymer emulsion, other monomer may be compolymerized in addition to the compound of the formula (A1) in such an amount that does not impair the adhesion ability and film strength of the polymer emulsion of the present invention. The above "other monomer" includes generally emulsion-polymerizable monomers. That is, the "other monomer" is selected from olefins such as ethylene, propylene and butene-1; vinyl halides such as vinyl chloride, vinylidene chloride and vinyl bromide; vinyl esters such as vinyl acetate and vinyl propinonate; vinyl ethers such as methyl vinyl ether, ethyl vinyl ether and isobutyl vinyl ether; alkenylbenzenes such as styrene, vinyltoluene, α-methylstyrene, chloromethylstyrene and stilbene; and vinyl cyanide compounds such as acrylonitrile and methacrylonitrile.

The so-produced polymer emulsion of the present invention exhibits excellent stability in water for a long period of time and can be also formed into a film which exhibits excellent adhesion to an adherend structure having a polyvalent cation reactive to a sulfonic acid group, since the emulsion polymer has a sulfonic acid unit.

Further, the polymer emulsion of the present invention is insoluble in water, so that a film formed therefrom is excellent in water resistance. Meanwhile, a film formed from a conventional water-soluble polymer having a sulfonic acid group or from an emulsion obtained by emulsion polymerizing a monomer in the presence of the conventional water-soluble polymer as an emulsifier is poor in water resistance, and it is not practical to use such a film under wet conditions in the mouth.

When the polymer emulsion is used as a film for the above-described purpose, the adhesion strength tends to decrease as the SO$_3$H group as a component forming the emulsion is neutralized. Therefore, preferably at least 50 mol %, more preferably at least 90 mol%, particularly preferably 100 mol %, of the —SO$_3$R group (R is a hydrogen atom, an alkali metal atom or an ammonium ion) is —SO$_3$H.

When the polymer emulsion of the present invention is used as an adhesive or a surface treating agent, it is preferred to use it in a state in which it is dispersed in a polar solvent such as water and an alcohol, e.g. as ethanol. In particular, when it is used for a dental purpose, it is preferred to use it in a dispersion in water or a water-ethanol mixed solvent. The solid content of the polymer emulsion in the above dispersing medium is generally 0.05 to 20% by weight, preferably 0.5 to 15% by weight.

For improving the reactivity of the above polymer emulsion with an adherend, a low molecular weight acid may be optionally added in such an amount that does not impair the stability of the emulsion and the water resistance of the film, i.e., in an amount of several to thousands in terms of ppm unit. The low molecular weight acid includes citric acid, oxalic acid, maleic acid, phosphoric acid and EDTA.

The above polymer emulsion may contain known additives as required, such as a coloring pigment, a loading pigment, an aggregate, a wetting agent and a thickener.

A film can be formed simply by applying the polymer emulsion of the present invention to an adherend having a polyvalent cation reactive with a sulfonic acid group, allowing it to stand for a few seconds to a few minutes and drying it with compressed air or the like at room temperature. It is assumed that the sulfonic acid group of each emulsion particle being oriented in the solvent direction chemically bonds to an adherend during the above process, whereby each emulsion particle bonds to the adherend.

Further, the dried film is completely removed from an adherend unreactive with a sulfonic acid group such as glass by washing it with water, while it is maintained on an adherend reactive with a sulfonic acid group such as hydroxyapatite even when it is washed with water. Therefore, formation of a film firmly bonded to a dentin can be attained, and it is suitable as a dentin protection film such as a sealing film against the hypersensitivity of a dentin. Further, this film can serve to bond an adherend to an acrylic resin, since it contains a poly(meth)acrylate component having high affinity to the acrylic resin.

The polymer emulsion of the present invention can be used in the following agents due to lrs properties and by employing an industrially usable treatment method: an antifogging agent, a drop removing agent, a filler for an ion adsorption column, an antistatic agent, an epoxy curing agent, a photoresist sealing agent, a sludge coagulating agent, a hardening agent for cements such as alumina cement, magnesium cement and Portland cement and gypsum, a reinforcement, a hardening agent for glass ionomer cement, zinc phosphate cement and a hydroxyapatite powder, an adhesive for bonding a structure which is reactive with the present emulsion to wood, an adhesive for wood used in house construction and a musical instrument, and a treating agent for coating paper.

The polymer emulsion of the present invention is, as described above, an emulsion of a copolymer containing recurring units of a sulfonic acid group and a (meth)acrylate, or an emulsion of a copolymer containing recurring units of a sulfonic acid group, a (meth)acrylate and either a carboxyl group or a phosphate ester group. Therefore, it can be formed into a film which exhibits adhesion to an adherend containing a polyvalent cation reactive with a sulfonic acid group. Further, it also exhibits excellent affinity to a radical-polymerizable acrylic resin. Since the formed film is firmly bonded to an adherend surface which can react with a sulfonic acid group, it is not removed by washing it with water. This film is useful as a dentin protection film, particularly useful against the hypersensitivity of a dentin. As will be described in Example 44 later, this film has been found to have an effect on at least 90% of volunteer patients, thus giving an excellent clinical result. When an attempt has been made to bond a hydroxyapatite structure to a material for remedy by using the polymer emulsion of the present invention, it has shown a maximum adhesion strength of 8,2 MPa, while commercially available materials (Comparative Examples 5 to 8) and linear (meth)acrylate/p-styrenesulfonic acid copolymers (without the procedures of washing with water) (Comparative Examples 9 and 10) have shown an adhesion strength of about 0 to 0.3 MPa. With the polymer emulsion of the present invention, the therapeutical treatment of the hypersensitivity of a dentin and the operation of a hydroxyapatite structure for remedy can be performed with simple procedures and with more reliability.

The present invention will be explained hereinafter more in detail by reference to Examples, which, however, shall not be limitative to the present invention.

In Examples, methyl methacrylate and acrylic acid were distilled under reduced pressure, and then dissolved oxygen was removed by degassing under nitrogen bubbling Just before use. Acid phosphooxyethyl methacrylate (Phosmer M, supplied by Unichemical Co., Ltd.) and sodium p-styrenesulfonate (Spinomer, purity 85%, supplied by Tosoh Corp.) were used as they were commercially available.

EXAMPLE 1 (E-1)

Distilled water (25 ml) was temperature-increased to 60° C., and a nitrogen gas was bubbled therein for 1 hour. Under nitrogen atmosphere, 1.0 g of methyl methacrylate (hereinafter referred to as "MMA"), 0.27 g of sodium p-styrenesulfonate (hereinafter referred to as "SSNa", Spinomer, supplied by Tosoh Corp.), and 30 mg of potassium persulfate and 10 mg of sodium hydrogen sulfite as polymerization initiators were added, and the mixture was vigorously stirred at 60° C. for 2 hours. 4.0 Grams of MMA, 1.1 g of SSNa, 70 mg of potassium persulfate and 20 mg of sodium phosphite were further added, and the mixture was vigorously stirred for 22 hours and then cooled to room temperature to give an emulsion having a solid content of 5.8 wt. %. Concentrated hydrochloric acid (0.47 ml) was added, and the mixture was stirred for 2 hours and then placed in a dialysis tube. The mixture was dialyzed in distilled water for 5 days while the distilled water was changed to new one each day. The dialysis tube was dried at room temperature under atmospheric pressure to give an emulsion having a solid content of 8.5 wt. %.

The infrared spectrum (IR) of the above-obtained emulsion polymer showed that it contained MMA and styrenesulfonic acid units. When the polymer was also analyzed with GPC using, as a reference, polymethyl methacrylate whose molecular weight was known, it had a number average molecular weight (Mn) of $1.0 \times 10^6$. Further, the elemental analysis of the polymer showed that the MMA unit content was 91.0 mol %.

EXAMPLE 2 (E-2)

Distilled water (32 ml) was temperature-increased to 60° C., and a nitrogen gas was bubbled therein for 1 hour. Under nitrogen atmosphere, 1.0 g of MMA, 0.16 g of SSNa, 30 mg of potassium persulfate and 10 mg of sodium hydrogen sulfite were added, and the mixture was vigorously stirred at 60° C. for 2 hours. Then, 1 g of MMA, 0.16 g of SSNa, 10 mg of potassium persulfate and 3 mg of sodium hydrogen sulfite were intermittently added six times at intervals of 30 minutes with the same components and amounts as described above each time, and the mixture was vigorously stirred for 19 hours. The reaction mixture was cooled to room temperature, and after 0.38 ml of concentrated hydrochloric acid was added, the mixture was fully stirred for 2 hours. The mixture was placed in a dialysis tube and dialyzed in distilled water for 5 days while the distilled water was changed to new one each day. The dialysis tube was dried at room temperature under atmospheric pressure to give an emulsion having a solid content of 10.7 wt. %.

The IR of the above emulsion polymer showed that it contained MMA and styrenesulfonic acid units. The polymer was analyzed in the same manner as in Example 1 to show Mn of $7.5 \times 10^5$. Further, the elemental analysis of the polymer showed that the MMA unit content was 94.1 mol %.

EXAMPLE 3 (E-3)

Distilled water (35 ml) was temperature-increased to 60° C., and a nitrogen gas was bubbled therein for 1 hour. Under nitrogen atmosphere, 1.0 g of MMA, 0.12 g of SSNa, 30 mg of potassium persulfate and 10 mg of sodium hydrogen sulfite were added, and the mixture was vigorously stirred at 60° C. for 2 hours. Then, 2.0 g of MMA, 0.24 g of SSNa, 30 mg of potassium persulfate and 10 mg of sodium hydrogen sulfite were added, and the mixture was vigorously stirred for 30 minutes. Then, 4.0 g of MMA, 0.48 g of SSNa, 60 mg of potassium persulfate and 20 mg of sodium hydrogen sulfite were added, and the mixture was vigorously stirred for 21.5 hours. The reaction mixture was cooled to room temperature, and after 0.29 ml of concentrated hydrochloric acid was added, the mixture was stirred for 2 hours. The mixture was placed in a dialysis tube and dialyzed in distilled water for 5 days while the distilled water was changed to new one each day. The dialysis tube was dried at room temperature under atmospheric pressure to give an emulsion having a solid content of 11.2 wt. %.

The IR of the above emulsion polymer showed that it contained MMA and styrenesulfonic acid units. The polymer was analyzed in the same manner as in Example 1 to show Mn of $6.2 \times 10^5$. Further, the elemental analysis of the polymer showed that the MMA unit content was 95.7 mol %.

EXAMPLE 4 (E-4)

Distilled water (41 ml) was temperature-increased to 60° C., and a nitrogen gas was bubbled therein for 1 hour. Under nitrogen atmosphere, 1.0 g of MMA, 0.08 g of SSNa, 30 mg of potassium persulfate and 10 mg of sodium hydrogen sulfite were added, and the mixture was vigorously stirred at 60° C. for 2 hours. Further, 2.0 g of MMA, 0.16 g of SSNa, 23 mg of potassium persulfate and 3 mg of sodium hydrogen sulfite were added three times at intervals of 30 minutes, and further, the mixture was vigorously stirred for 21.5 hours. The reaction mixture was cooled to room temperature, and after 0.19 ml of concentrated hydrochloric acid was added, the mixture was stirred for 2 hours. The mixture was placed in a dialysis tube and dialyzed in distilled water for 5 days while the distilled water was changed to new one each day. The dialysis tube was dried at room temperature under atmospheric pressure to give an emulsion having a solid content of 16.9 wt. %.

The IR of the above emulsion polymer showed that it contained MMA and styrenesulfonic acid units. The polymer was analyzed in the same manner as in Example 1 to show Mn of $5.9 \times 10^5$. Further, the elemental analysis of the polymer showed that the MMA unit content was 96.7 mol %.

EXAMPLE 5 (E-5)

Distilled water (55 ml) was temperature-increased to 60° C., and a nitrogen gas was bubbled therein for 1 hour. Under nitrogen atmosphere, 1.0 g of MMA, 0.06 g of SSNa, 30 mg of potassium persulfate and 10 mg of sodium hydrogen sulfite were added, and the mixture was vigorously stirred at 60° C. for 2 hours. Further, 2.0 g of MMA, 0.12 g of SSNa, 23 mg of potassium persulfate and 3 mg of sodium hydrogen sulfite were added three times at intervals of 30 minutes, and further, the mixture was vigorously stirred for 21.5 hours. The resultant emulsion had a solid content of 8.8 wt. %. The emulsion was cooled to room temperature, and after 0.14 ml of concentrated hydrochloric acid was added, the mixture was stirred for 2 hours. The mixture was placed in a dialysis tube and dialyzed in distilled water for 5 days while the distilled water was changed to new one each day. The dialysis tube was dried at room temperature under atmospheric pressure to give an emulsion having a solid content of 14.7 wt. %.

The IR of the above emulsion polymer showed that it contained MMA and styrenesulfonic acid units. The polymer was analyzed in the same manner as in Example 1 to show Mn of $1.6 \times 10^6$. Further, the elemental analysis of the polymer showed that the MMA unit content was 97.6 mol %.

EXAMPLE 6 (E-6)

Distilled water (50 ml) was temperature-increased to 60° C., and a nitrogen gas was bubbled therein for 1 hour. Under nitrogen atmosphere, 2.0 g of MMA, 1.2 g of SSNa, 30 mg of potassium persulfate and 10 mg of sodium hydrogen sulfite were added, and the mixture was vigorously stirred at 60° C. for 2.5 hours. Further, 1.0 g of MMA, 15 mg of potassium persulfate and 7 mg of sodium hydrogen sulfite were added four times at intervals of 30 minutes, and further, the mixture was vigorously stirred for 19.5 hours. The reaction mixture was cooled to room temperature, and after 0.4 ml of concentrated hydrochloric acid was added, the mixture was stirred for 2 hours. The mixture was placed in a dialysis tube and dialyzed in distilled water for 5 days while the distilled water was changed to new one each day. The dialysis tube was dried at room temperature under atmospheric pressure to give an emulsion having a solid content of 9.1 wt. %.

The elemental analysis of the polymer showed that the MMA unit content was 92.6 mol %.

EXAMPLE 7 (E-7)

Distilled water (50 ml) was temperature-increased to 60° C., and a nitrogen gas was bubbled therein for 1 hour. Under nitrogen atmosphere, 2.0 g of MMA, 0.54 g of SSNa, 30 mg of potassium persulfate and 10 mg of sodium hydrogen sulfite were added, and the mixture was vigorously stirred at 60° C. for 2.5 hours. Further, 1.0 g of MMA, 15 mg of potassium persulfate and 7 mg of sodium hydrogen sulfite were added four times at intervals of 30 minutes, and further, the mixture was vigorously stirred for 19.5 hours. The reaction mixture was cooled to room temperature, and after 0.19 ml of concentrated hydrochloric acid was added, the mixture was stirred for 2 hours. The mixture was placed in a dialysis tube and dialyzed in distilled water for 5 days while the distilled water was changed to new one each day. The dialysis tube was dried at room temperature under atmospheric pressure to give an emulsion having a solid content of 10.9 wt. %.

The elemental analysis of the polymer showed that the MMA unit content was 96.9 mol %. This polymer emulsion was observed through a transmission microscope to show that it contains particles having a diameter of 0.1 to 0.5 μm.

EXAMPLE 8 (E-8)

Distilled water (50 ml) was temperature-increased to 60° C., and a nitrogen gas was bubbled therein for 1 hour. Under nitrogen atmosphere, 2.0 g of MMA, 0.48 g of SSNa, 30 mg of potassium persulfate and 10 mg of sodium hydrogen sulfite were added, and the mixture was vigorously stirred at 60° C. for 2 hours. Further, 1.0 g of MMA, 15 mg of potassium persulfate and 7 mg of sodium hydrogen sulfite were added four times at intervals of 30 minutes, and further, the mixture was vigorously stirred for 20 hours. The reaction mixture was cooled to room temperature, and after 0.17 ml of concentrated hydrochloric acid was added, the mixture was stirred for 2 hours. The mixture was placed in a dialysis tube and dialyzed in distilled water for 5 days while the distilled water was changed to new one each day. The dialysis tube was dried at room temperature under atmospheric pressure to give an emulsion having a solid content of 10.5 wt. %.

The elemental analysis of the polymer showed that the MMA unit content was 98.5 mol %.

EXAMPLE 9 (EA-1)

While 60 ml of a hydrochloric acid aqueous solution having pH of 2 was temperature-increased to 60° C., an argon gas was bubbled therein for 20 minutes. Under argon atmosphere, 2.00 g (20 mmol) of MMA, 0.24 g (3.3 mmol) of acrylic acid (hereinafter referred to as "AA"), 0.61 g (2.5 mmol) of SSNa, 30 mg of potassium persulfate (hereinafter referred to as "KPS") and 10 mg of sodium hydrogen sulfite (hereinafter referred to as "NHS") were added, and the mixture was vigorously stirred at 60° C. for 2.5 hours. 15 Minutes after the monomers had been added, the mixture became a bluish white solution.

Further, 1.00 g (10 mmol) of MMA, 30 mg of KPS and 15 mg of NHS were added, and then 1 g of MMA was added three times at intervals of 20 minutes. After 30 mg of KPS and 15 mg of NHS had been added, the mixture was stirred until the total reaction time was as long as 24 hours. The reaction mixture was cooled to room temperature, and after 0.21 ml of concentrated hydrochloric acid was added, the mixture was further stirred for 2 hours. The mixture was placed in a dialysis tube and dialyzed in distilled water for 7 days while the distilled water was changed to new one each day to give an emulsion having a solid content of 5.7wt. %.

The IR of the above emulsion polymer showed that it contained MMA, AA and styrenesulfonic acid (hereinafter referred to as "SSA") units. Further, the elemental analysis (hereinafter referred to as "EA") of the polymer showed that the SSA and AA unit contents were 7.2 and 13.1 mol%, respectively.

EXAMPLE 10 (EA-2)

While 70 ml of a hydrochloric acid aqueous solution having pH of 2 was temperature-increased to 60° C., an argon gas was bubbled therein for 20 minutes. Under argon atmosphere, 2.00 g (20 mmol) of MMA, 0.24 g (3.3 mmol) of AA, 0.29 g (1.2 mmol) of SSNa, 30 mg of KPS and 10 mg of NHS were added, and the mixture was vigorously stirred for 2.5 hours. 15 Minutes after the monomers had been added, the mixture became a bluish white solution.

Further, 1.00 g (10 mmol) of MMA, 30 mg of KPS and 15 mg of NHS were added, and then 1 g of MMA was added three times at intervals of 20 minutes. After 30 mg of KPS and 15 mg of NHS had been added, the mixture was stirred until the total reaction time was as long as 24 hours. The reaction mixture was cooled to room temperature, and after 0.10 ml of concentrated hydrochloric acid was added, the mixture was further stirred for 2 hours. The mixture was placed in a dialysis tube and dialyzed in distilled water for 7 days while the distilled water was changed to new one each day to give an emulsion having a solid content of 8.1 wt. %.

The IR of the above emulsion polymer showed that it contained MMA, SSA and AA units. Further, the EA of the polymer showed that the SSA and AA unit contents were 3.2 and 27.8 mol %, respectively.

EXAMPLE 11 (EA-3)

While 70 ml of a hydrochloric acid aqueous solution having pH of 2 was temperature-increased to 60° C., an argon gas was bubbled therein for 20 minutes. Under argon atmosphere, 2.00 g (20 mmol) of MMA, 0.24 g (3.3 mmol) of AA, 0.17 g (0.7 mmol) of SSNa, 30 mg of KPS and 10 mg of NHS were added, and the mixture was vigorously stirred for 2.5 hours. 15 Minutes after the monomers had been added, the mixture became a bluish white solution.

Further, 1.00 g (10 mmol) of MMA, 30 mg of KPS and 15 mg of NHS were added, and then 1 g of MMA was added three times at intervals of 20 minutes. After 30 mg of KPS and 15 mg of NHS had been added, the mixture was stirred until the total reaction time was as long as 24 hours. The reaction mixture was cooled to room temperature, and after 0.06 ml of concentrated hydrochloric acid was added, the mixture was further stirred for 2 hours. The mixture was placed in a dialysis tube and dialyzed in distilled water for 7 days while the distilled water was changed to new one each day to give an emulsion having a solid content of 5.6wt. %.

The IR of the above emulsion polymer showed that it contained MMA, SSA and AA units.

EXAMPLE 12 (EP-1)

While 70 ml of distilled water was temperature-increased to 60° C., an argon gas was bubbled therein for 20 minutes. Under argon atmosphere, 2.00 g (20 mmol) of MMA, 0.71 g (3.4 mmol) of Phosmer M, 0.63 g (2.6 mmol) of SSNa, 30 mg of KPS and 10 mg of NHS were added, and the mixture was vigorously stirred for 3 hours. 20 Minutes after the monomers had been added, the mixture became a bluish white solution.

Further, 1.00 g (10 mmol) of MMA, 30 mg of KPS and 15 mg of NHS were added, and then 1 g of MMA was added three times at intervals of 20 minutes. After 30 mg of KPS and 15 mg of NHS had been added, the mixture was stirred until the total reaction time was as long as 24 hours. The reaction mixture was cooled to room temperature, and after 0.22 ml of concentrated hydrochloric acid was added, the mixture was further stirred for 2 hours. The mixture was placed in a dialysis tube and dialyzed in distilled water for 7 days while the distilled water was changed to new one each day to give an emulsion having a solid content of 7.1 wt. %.

The IR of the above emulsion polymer and the analysis thereof with an X-ray light electron analyzing apparatus (supplied by Shimadzu Corporation, hereinafter referred to as "ESCA") showed that it contained MMA, SSA and Phosmer M. Further, the EA of the polymer showed that the SSA and Phosmer M unit contents were 8.0 and 16.1 mol %, respectively.

EXAMPLE 13 (EP-2)

While 70 ml of distilled water was temperature-increased to 60° C., an argon gas was bubbled therein for 20 minutes. Under argon atmosphere, 2.00 g (20 mmol) of MMA, 0.74 g (3.5 mmol) of Phosmer M, 0.30 g (1.2 mmol) of SSNa, 30 mg of KPS and 10 mg of NHS were added, and the mixture was vigorously stirred for 3 hours. 10 Minutes after the monomers had been added, the mixture became a bluish white solution.

Further, 1 g (10 mmol) of MMA, 30 mg of KPS and 10 mg of NHS were added, and then 1 g of MMA was added three times at intervals of 20 minutes. After 30 mg of KPS and 10 mg of NHS had been added, the mixture was stirred until the total reaction time was as long as 24 hours. The reaction mixture was cooled to room temperature, and after 0.10 ml of concentrated hydrochloric acid was added, the mixture was further stirred for 2 hours. The mixture was placed in a dialysis tube and dialyzed in distilled water for 7 days while the distilled water was changed to new one each day to give an emulsion having a solid content of 6.2 wt. %.

The IR and ESCA of the above emulsion polymer showed that it contained MMA, SSA and Phosmer M. Further, the EA of the polymer showed that the SSA and Phosmer M unit contents were 5.3 and 2.7 mol %, respectively.

EXAMPLE 14 (EP-3)

While 70 ml of distilled water was temperature-increased to 60° C., an argon gas was bubbled therein for 20 minutes. Under argon atmosphere, 2.00 g (20 mmol) of MMA, 0.65 g (3.1 mmol) of Phosmer M, 0.17 g (0.7 mmol) of SSNa, 30 mg of KPS and 10 mg of NHS were added, and the mixture was vigorously stirred for 3 hours. 5 Minutes after the monomers had been added, the mixture turned bluish white.

Further, 1 g (10 mmol) of MMA, 30 mg of KPS and 10 mg of NHS were added, and then 1 g of MMA was added three times at intervals of 20 minutes. After 30 mg of KPS and 10 mg of NHS had been added, the mixture was stirred until the total reaction time was as long as 24 hours. The reaction mixture was cooled to room temperature, and after 0.06 ml of concentrated hydrochloric acid was added, the mixture was further stirred for 2 hours. The mixture was placed in a dialysis tube and dialyzed in distilled water for 7 days while the distilled water was changed to new one each day to give an emulsion having a solid content of 6.5 wt. %.

The IR and ESCA of the above emulsion polymer showed that it contained MMA, SSA and Phosmer M. Further, the EA of the polymer showed that the SSA and Phosmer M unit contents were 2.5 and 7.7 mol %, respectively.

COMPARATIVE EXAMPLE 1

All the monomers used in Example 1 were added at one time. That is, 25 ml of distilled water was temperature-increased to 60° C., and a nitrogen gas was bubbled therein for 1 hour. Under nitrogen atmosphere, 5.0 g of MMA, 1.37 g of SSNa, 100 mg of potassium persulfate and 30 mg of sodium hydrogen sulfite were added at once. In this case, a large amount of aggregates were formed, and no emulsion was obtained.

COMPARATIVE EXAMPLE 2

The emulsion polymerization was carried out in the same manner as in Example 9 except that AA was replaced with sodium acrylate (hereinafter referred to as "ANa"). That is, while 60 ml of distilled water was temperature-increased to 60° C., an argon gas was bubbled therein for 20 minutes.

Under argon atmosphere, 2.00 g (20 mmol) of MMA, 0.28 g (3 mmol) of ANa, 0.61 g (2.5 mmol) of SSNa, 30 mg of KPS and 10 mg of NHS were added, and the mixture was vigorously stirred at 60° C.. After 20 minutes., a large amount of aggregates were formed, and no emulsion was obtained.

COMPARATIVE EXAMPLE 3

The same emulsion polymerization as that of Example 9 was carried out in distilled water. That is, while 60 ml of distilled water was temperature-increased to 60° C., an argon gas was bubbled therein for 20 minutes. Under argon atmosphere; 2.00 g (20 mmol) of MMA, 0.24 g (3 mmol) of AA, 0.61 g (2.5 mmol) of SSNa, 30 mg of KPS and 10 mg of NHS were added, and the mixture was vigorously stirred at 60° C.. Since the formation of a large amount of aggregates was observed after 15 minutes, the reaction was discontinued.

COMPARATIVE EXAMPLE 4 (EMMA)

While 50 ml of distilled water was temperature-increased to 60° C., an argon gas was bubbled therein for 20 minutes. Then, 250 mg of sodium laurylsulfate was added, and the mixture was fully stirred. Thereafter, 10 g (0.1 mol) of MMA, 100 mg of KPS and 10 mg of NHS were added, and the monomers were polymerized for 5 hours. The resultant product was cooled to room temperature, placed in a dialysis tube and dialyzed in distilled water for 7 days while the distilled water was changed to new one each day to give an emulsion having a solid content of 15.7 wt. %.

EXAMPLES 15–24

Fresh emulsion bovine teeth were polished in water with a water-resistant emery paper (#600) to expose enamels or dentins. Adhesion surfaces were defined by masking tapes having a hole whose diameter was 5.4 mm. Each of the polymer emulsions (E-1 to E-8) obtained in Examples 1 to 8 was adjusted to a solid content of 5 wt. %, and then applied to the adhesion surface in an amount of 3 μl. The applied emulsions were allowed to stand for 1 minutes, and lightly blown by compressed air to form films. MMA was softly applied to the resultant adhesion surfaces twice with a dental brush. Then, acryl rods having a diameter of 6 mm were planted thereon with an MMA-tri-n-butylborane (TBB) resin (X) whose TBB was a polymerization catalyst, and allowed to stand at room temperature for 1 hour to cure the resin. The teeth with the acryl rods planted thereon were immersed in water at 37° C. for 24 hours and measured for adhesion strength by subjecting them to a tensile test using an autograph. (supplied by Shimadzu Corporation) with a cross head speed of 2 mm/min.

The above procedures after the film formation were repeated using a spontaneous polymerization resin (Y) containing BPO-p-toluldine as a catalyst (Methafast, supplied by Sun Medical Co., Ltd), to measure adhesion strength in the same manner as above.

Further, films were formed in the same manner as above, and a bonding agent (Z) containing 0.5 wt. % of d,l-camphorquinone, 0.5 wt. % of diethylaminobenzoic acid and 99.0 wt. % of triethylene glycol dimethacrylate was applied in an amount of 10 μl and exposed to light from a visible light irradiator (Translux, supplied by Kulzer) for 20 seconds. Then, acryl rings having an internal diameter of 6 mm and a height of 1 mm were placed thereon, and Photobright US (supplied by Kuraray Co., Ltd.) was filled within the ring-formed circles and further exposed to light for 1 minute. Acryl rods were planted with Methafast, and measured for adhesion strength in the same manner as above. Table 1 shows the results.

TABLE 1

| Example | Emulsion (concentration of 5 wt. %) Code | Dental resin* | Bovine teeth Enamel (EN)/ Dentin (DE) | Adhesion strength (MPa) |
|---|---|---|---|---|
| 15 | E-1 | X | EN | 3.1 |
| 16 | E-2 | X | EN | 1.1 |
| 17 | E-3 | X | EN | 1.8 |
| 18 | E-5 | X | EN | 2.3 |
| 19 | E-7 | X | EN | 8.2 |
| 20 | E-7 | X | DE | 2.6 |
| 21 | E-7 | Y | EN | 2.5 |
| 22 | E-7 | Z | EN | 4.0 |
| 23 | E-7 | Z | DE | 1.0 |
| 24 | E-6 | X | EN | 2.3 |
| Blank | No adhesive film | X | EN | 1.0 |
|  | No adhesive film | X | DE | 0 |
|  | No adhesive film | X | EN | 0 |
|  | No adhesive film | Y | DE | 0 |
|  | No adhesive film | Y | EN | 0.7 |

*Notes)
X: MMA-TBB resin
Y: MMA-BPO-DMPT resin
X: 3G-CQ-DEABA resin

EXAMPLES 25–30

Emulsions obtained in Examples (EA-1 to EA-3 and EP-1 to EP-3) were adjusted to a solid content of 5 wt. %, and measured for adhesion strength to enamel in the presence of an MMA/TBB resin (X) in the same manner as above. Table 2 shows the results.

TABLE 2

| Example | Emulsion (concentration of 5 wt. %) Code | Dental resin* | Bovine teeth Enamel (EN)/ Dentin (DE) | Adhesion strength (MPa) |
|---|---|---|---|---|
| 25 | EA-1 | X | EN | 3.0 |
| 26 | EA-2 | X | EN | 2.4 |
| 27 | EA-3 | X | EN | 2.4 |
| 28 | EP-1 | X | EN | 3.4 |
| 29 | EP-2 | X | EN | 2.5 |
| 30 | EP-3 | X | EN | 3.4 |

*Note:
X: MMA-TBB resin

COMPARATIVE EXAMPLES 5–8

Fresh emulsion bovine teeth were polished in water with water-resistant emery paper up to #600. The tooth surface areas were defined by masking tapes having a hole whose diameter was 5.4 mm. Further, acryl rings having an internal diameter of 6 mm and a height of 1 mm were placed thereon, and a commercially available polymer cement was applied within the ring-formed circles and cured. Then, an MMA-TBB resin was filled therein, and the polymer cement was measured for adhesion strength in the same manner as above. The polymer cement was prepared from Hybond Glass Ionomer (HYG, supplied by Shofusha) or Ketac cement (KC, supplied by ESPE) in accordance with the methods specified by each supplier. Table 3 shows the results.

COMPARATIVE EXAMPLES 9–10

The tensile test was carried out by using an MMA/p-styrenesulfonic acid copolymer disclosed in Japanese Laid-Open Patent Publication No.171,024/1985, i.e., a linear MMA-p-styrenesulfonic acid polymer obtained by reacting MMA with SSNa in a water/ethanol-containing solvent and post-treating the resultant reaction product. That is, the copolymer having an MMA content of 70 mol % (MS-7) and the copolymer having an MMA content of 90 mol % (MS-9) were prepared and measured for adhesion strength using a MMA-TBB resin (X) in the same manner as above. Table 3 shows the results.

TABLE 3

| Comp. Example | Polymer cement and MS | Dental resin* | Bovine teeth Enamel (EN)/ Dentin (DE) | Adhesion strength (MPa) |
|---|---|---|---|---|
| 5 | HYG | X | EN | 0.1 |
| 6 | KC | X | EN | 0.3 |
| 7 | HYG | X | DE | 0 |
| 8 | KC | X | DE | 0.2 |
| 9 | MS-7 | X | DE | 0 |
| 10 | MS-9 | X | DE | 0.3 |

*Note:
X: MMA-TBB resin

EXAMPLE 31

The latex (E-7) having a concentration of 0.05 wt. % was applied to an enamel and dentin, allowed to stand for 1 minute and dried with air. The resultant film was washed with water for 30 minutes, dried and observed through a scanning electron microscope (JMS-5400, JEOL) at an acceleration voltage of 30 KV to show that the film remained on the surfaces, i.e., that the film did not come off when washed with water, since it bonded to the adherends. An adhesion strength to the enamel was 2.0 MPa when MMA-TBB was used as a bonding agent.

COMPARATIVE EXAMPLE 11

A glass surface used as an adhesion surface under the same conditions as those in Example 31 was observed to show no residual film, i.e., that the film completely came off when washed with water.

EXAMPLES 32–37

The surfaces of synthetic hydroxyapatite having a diameter of 3 mm (supplied by Pentax, hereinafter referred to as "HAP") were fully cleaned. The emulsions obtained in Examples (EA-1–EA-3 and EP-1–EP-3) were respectively adjusted to a solid content of 5 wt. %, and applied to HAP surfaces in an amount of 1 µl. The applied emulsions were allowed to stand for 1 minute, and lightly blown by compressed air to form films. The films were washed with water for 1 minute and dried. Each film was evaluated for a residual ratio by examining C/Ca before the latices were applied and C/Ca after the films were washed with water by means of an X-ray light electron analyzing apparatus ESCA 500 supplied by Shimadzu Corporation, and calculated a ratio ($C_1$) of C/Ca's.

Table 4 shows the results.

COMPARATIVE EXAMPLE 12

Example 32 was repeated except that the emulsion was replaced with EMMA obtained in Comparative Example 4 and C/Ca ratio of the resultant film was calculated. Table 4 shows the results.

TABLE 4

| Example | Emulsion (concentration of 5 wt. %) Code | $C_1$* |
|---|---|---|
| 32 | EA-1 | 7.6 |
| 33 | EA-2 | 4.7 |
| 34 | EA-3 | 5.0 |
| 35 | EP-1 | 4.0 |
| 36 | EP-2 | 4.2 |
| 37 | EP-3 | 5.4 |
| Comparative Example 12 | EMMA | 0.8 |

*Note
$C_1 = \dfrac{\text{C/Ca (film washed with water)}}{\text{C/Ca (HAP surface)}}$

EXAMPLES 38–43

While water was poured, fresh emulsion bovine teeth were polished with water-resistant emery paper (#600) to expose enamels. The emulsions obtained in Examples (EA-1 to EA-3 and EP-1 to EP-3) were adjusted to a solid content of 5 wt. %, and applied to adhesion surfaces in the amount of 1 µl. The applied emulsions were allowed to stand for 1 minute and, lightly blown with compressed air to form films. The films were washed with water for 1 minute, dried and observed through a scanning electron microscope (JMS-5400, JEOL) at an acceleration voltage of 10 KV to show that all the films remained and that no film came off.

EXAMPLE 44

The E-7 emulsion was adjusted to a solid content of 5 wt. %, and applied to sixteen hypersensitive volunteer patients after approval by them. That is, their diseased parts were cleaned, and the emulsion was applied thereto with tampons, allowed to stand and dried with air. Fifteen patents out of the sixteen had a good effect and had no relapse for at least 6 months.

EXAMPLE 45

(1) Calcium chloride was added to E-7 emulsion having a solid content of 5 wt. % such that the amount of the calcium chlorlde based on the sulfonic acid group of the E-7 emulsion was 3 equivalent weights. The mixture was shaken for 30 seconds and subjected to centrifugal separation at 1,600 rpm for 10 minutes. The supernatant showed no MS emulsion, and all the contents coagulated.

(2) The above procedures (1) were repeated except that the 3 equivalent weight calcium chloride was replaced with a 1 equivalent weight aluminum chloride. The supernatant showed no MS emulsion, and all the contents coagulated.

(3) E-7 emulsion having a solid content of 5 wt. % was subjected to centrifugal separation at 1.600 rpm for 10 seconds to show no coagulation.

EXAMPLE 46

The surfaces of synthetic hydroxyapatite pellets having a diameter of 10 mm and a diameter of 4 mm were cleaned under water current with water-resistant emery paper #600. At room temperature, E-6 emulsion having a solid content of 8 wt. % was applied to the synthetic hydroxyapatite pellet having a diameter of 10 mm, and immediately thereafter, the synthetic hydroxyapatite pellet having a diameter of 4 mm was bonded thereto. The pellets were allowed to stand at room temperature for 12 hours as they were, and then a rod was planted on the synthetic hydroxyapatite pellet having a diameter of 4 mm in the presence of an instantaneous adhesive. Then, the pellets were subjected to a tensile test with an autograph at a cross head speed of 2 mm/min. to show an adhesion strength of 24 kgf/cm$^2$. It is seen that hydroxyapatite pellets can be bonded to each other in the presence of the emulsion of the present invention.

For comparison, the above procedures were repeated except that the E-6 emulsion was replaced with EMMA (Comparative Example 4). As a result, the adhesion strength was 0 kgf/cm$^2$, and it is seen that hydroxyapatite pellets cannot be bonded to each other in the presence of EMMA.

EXAMPLE 47 (E-9)

An emulsion containing 5% by weight of a polymer having —SO$_3$H group was obtained in the same manner as in Example 1. This emulsion in an amount of 50 ml was vigorously stirred at 500 rpm while increasing the temperature of the emulsion up to 80° C. under a nitrogen gas current. 1.0 Gram of methyl methacrylate (MMA), 30 mg of potassium persulfate and 10 mg of sodium hydrogen sulfite were added, and the mixture was stirred at 500 rpm for 30 minutes. Further, 1.0 g of MMA, 30 mg of potassium persulfate and 10 mg of sodium hydrogen sulfite were added, and the mixture was further stirred for 20 hours. After the reaction, the reaction product was placed in a dialysis tube and dialyzed for 5 days while changing distilled water each day. Then, the dialysis tube was dried at room temperature under atmospheric pressure to give an emulsion having a solid content of 8.0 wt. %. During the polymerization and the dialyzing, the emulsion did not show any aggregation. The emulsion was observed by means of a scanning electron microscope (SEM) to show that it had particles having a diameter of 0.1 to 0.5 μm.

EXAMPLE 48 (EA-4)

While 60 ml of a hydrochloric acid aqueous solution having a pH of 2 was temperature-increased to 60° C., an argon gas was bubbled for 20 minutes. Under argon gas atmosphere, 2 g of methyl methacrylate, 0.2 g of acrylic acid, 0.61 g of sodium p-styrenesulfonate, 30 mg of potassium persulfate and 10 mg of sodium hydrogen sulfite were added. The mixture became a bluish white solution 15 minutes after the addition of the monomers. After a total reaction time of 24 hours, the reaction mixture was cooled to room temperature, and 0.21 ml of concentrated hydrochloric acid was added. The mixture was stirred for 2 hours, then placed in a dialysis tube, and dialyzed in distilled water for 7 days while the distilled water was changed to new one each day. After the dialysis, the mixture was concentrated at room temperature to a solid content of 5% by weight to give an emulsion having an excellent dispersion state.

While 30 ml of the above emulsion was temperature-increased to 60° C., an argon gas was bubbled for 20 minutes. Then, 0.5 g of methyl methacrylate, 15 mg of potassium persulfate and 8 mg of sodium hydrogen sulfite were added, and after 20 minutes, 0.5 g of methyl methacrylate, 15 mg of potassium persulfate and 8 mg of sodium hydrogen sulfite were further added. After a total reaction time of 24 hours, the reaction was terminated to give an emulsion having a solid content of 7% by weight. The emulsion showed an excellent dispersion state, and no aggregation was found.

EXAMPLE 49 (EP-4)

While 70 ml of distilled water was temperature-increased to 60° C., an argon gas was bubbled for 20 minutes. Under argon gas atmosphere, 2 g of methyl methacrylate, 0.71 g of Phosmer M, 0.63 g of sodium p-styrenesulfonate, 30 mg of potassium persulfate and 10 mg of sodium hydrogen sulfite were added. The mixture became a bluish white solution 15 minutes after the addition of the monomers. After a total reaction time of 24 hours, the reaction mixture was cooled to room temperature, and 0.22 ml of concentrated hydrochloric acid was added. The mixture was stirred for 2 hours, then placed in a dialysis tube and dialyzed in distilled water for 7 days while the distilled water was changed to new one each day. After the dialysis, the mixture was concentrated at room temperature to a solid content of 5% by weight to give an emulsion having an excellent dispersion state.

While 30 ml of the above emulsion was temperature-increased to 60° C., an argon gas was bubbled for 20 minutes. Then, 0.5 g of methyl methacrylate, 15 mg of potassium persulfate and 8 mg of sodium hydrogen sulfite were added. After 20 minutes, 0.5 g of methyl methacrylate, 15 mg of potassium persulfate and 8 mg of sodium hydrogen sulfite were added. After a total reaction time of 24 hours, the reaction was terminated to give an emulsion having a solid content of 7% by weight. The emulsion showed an excellent dispersion state, and no aggregation was found.

COMPARATIVE EXAMPLE 13 (E-10)

While 410 ml of distilled water was temperature-increased to 60° C., an argon gas was bubbled for 20 minutes. Under argon gas atmosphere, 3 g (30 mmol) of MMA, 16.9 g (70 mol) of SSNa, 0.27 g of potassium persulfate (KPS) and 0.13 g of sodium hydrogen sulfite (NHS) were added, and the mixture was vigorously stirred for 2 hours. Then, 1 g (10 mmol) of MMA, 28 mg of KPS and 14 g of NHS were added, and after 20 minutes, 1 g (10 mmol) of MMA, 28 mg of KPS and 14 mg g of NHS were further added, and after a total reaction time of 7 hours, the reaction mixture was cooled to room temperature. Then, 5.83 ml of concentrated hydrochloric acid was added, and the mixture was further stirred for 2 hours, then placed in a dialysis tube and dialyzed in distilled water for 7 days while the distilled water was changed to new one each day. After the dialysis, the mixture was concentrated at room temperature to a solid content of 5% by weight. The polymer obtained in the presence of MMA:SSNa (=30:70 mol %) as an emulsifier, and the polymer converted to an acid type, as above did not become opaque, and they were soluble in water.

EXAMPLE 50 (E-11)

While 232 ml of distilled water was temperature-increased to 60° C., an argon gas was bubbled for 20 minutes. Under argon gas atmosphere, 3 g (30 mmol) of MMA, 7.2 g (30 mmol) of SSNa, 140 mg of potassium persulfate (KPS) and 47 mg of sodium hydrogen sulfite (NHS) were added, and the mixture was vigorously stirred. Then, 1 g (10 mmol)

of MMA, 28 mg of KPS and 14 mg of NHS were added, and after 20 minutes, 1 g (10 mmol) of MMA, 28 mg of KPS and 14 mg of NHS were further added. After a total reaction time of 7 hours, the reaction mixture was cooled to room temperature, and 2.5 ml of concentrated hydrochloric acid was added. The mixture was stirred for 2 hours, then placed in a dialysis tube and dialyzed in distilled water for 7 days while the distilled water was changed to new one each day. After the dialysis, the mixture was concentrated at room temperature to a solid content of 5% by weight. The polymer obtained in the presence of MMA:SSNa (=50:50 mol %) as an emulsifier, and the polymer converted to an acid type, as above became opaque, and they were emulsions of an emulsion polymer stably dispersed in water.

EXAMPLE 51 (E-12)

While 154 ml of distilled water was temperature-increased to 60° C., an argon gas was bubbled for 20 minutes. Under argon gas atmosphere, 3 g (30 mmol) of MMA, 3.1 g (12.8 mmol) of SSNa, 84 mg of potassium persulfate (KPS) and 28 mg of sodium hydrogen sulfite (NHS) were added, and the mixture was vigorously stirred. Then, 1 g (10 mmol) of MMA, 28 mg of KPS and 14 mg of NHS were added, and after 20 minutes, 1 g (10 mmol) of MMA, 28 mg of KPS and 14 mg of NHS were added. After a total reaction time of 7 hours, the reaction mixture was cooled to room temperature, and 1.1 ml of concentrated hydrochloric acid was added. The mixture was stirred for 2 hours, then placed in a dialysis tube and dialyzed in distilled water for 7 days while the distilled water was changed to new one each day. After the dialysis, the mixture was concentrated at room temperature to a solid content of 5% by weight. The polymer obtained in the presence of MMA:SSNa (=70:30 mol %) as an emulsifier, and the polymer converted to an acid type, as above became opaque, and they were emulsions of an emulsion polymer stably dispersed in water.

EXAMPLE 52

Fresh emulsion bovine teeth were polished in water with a water-resistant emery paper (#600), and the so-polished enamels were defined with masking tapes having a diameter of 5.4 mm. The emulsions of the emulsion polymers E-11 and E-12 and the water-soluble polymer E-10 were respectively applied to the adhesion surfaces (defined surfaces) in an amount of 3 μl each. The applied emulsions were allowed to stand for 1 minute, and slightly blown with compressed air to form films. Acryl rods having a diameter of 6 mm were planted on the film-formed surfaces with an MMA-TBB resin, and allowed to stand for 1 hour. The bovine teeth with the acryl rods planted thereon were immersed in water at 37° C. for 24 hours, and measured for adhesion strength by a tensile test at a cross head speed of 2 mm/minute. The films formed from E-10, E-11 and E-12 showed adhesion strengths of 1.0, 1.5 and 2.0 Mpa, respectively. The film formed from E-11 showed the lowest value of 1.0 MPA. Table 5 shows the results.

COMPARATIVE EXAMPLE 14

Sodium hydrogencarbonate was added to each of E-10, E-11, E-12 and the emulsion of E-7 adjusted to a concentration of 5% so that they were rendered neutral or sulfonic acid groups were converted to sodium sulfonates. The resultant emulsions are referred to as E-10/Na, E-11/Na, E-12/Na and E-7/Na. These emulsions were tested for adhesion in the same manner as in Example 52. All the films formed from the above emulsions showed adhesion strengths of 0 MPa.

Table 5 shows the results.

EXAMPLE 53

Fresh emulsion bovine teeth were polished in water with a water-resistant emery paper (#600) to expose dentins, and the dentins were polished with a tooth brush with a tooth paste (Apadent A, supplied by Japan Apatite Limited) for 3 minutes. The bovine teeth were washed with water, and ultrasonically treated in water for 30 minutes to clean the dental tubules of smear plugs. The resultant bovine teeth were used as model surfaces for cervical hyperesthesia. E-7, EA-1, EP-1, E-10, E-11, E-12, E-7/Na, E-10/Na, E-11/Na and E-12/Na were adjusted to a solid content of 5% by weight, and applied to model surfaces with a sponge. After 30 seconds, the model surfaces were slightly blown with compressed air to form films. The film-formed surfaces were washed with water for 1 minute. And, their SEM photographs (×2,000) were taken, and the dental tubules sealing ratio was determined.

Dental tubules sealing ratio (%)=(number of dental tubules sealed with emulsion/total number of dental tubules)×100

The results were that E-7 (80%), (EA-1 (72 %), EP-1 (75%), E-10 (10%), E-11 (52%) and E-12 (65 %), and it was found that E-10 was inferior in sealability since its dental tubules sealing ratio was and almost all dental tubules remained open. Further, E-7/Na, E-10/Na, E-11/Na and E-12/Na showed dental tubules sealing ratios of 0%.

Table 5 shows the results.

TABLE 5

| Emulsion No. | Tensile adhesion strength (MPa) | Dental tubules sealing ratio (%) |
| --- | --- | --- |
| E-7 | 8.2 | 80 |
| E-11 | 1.5 | 52 |
| E-12 | 2.0 | 62 |
| EA-1 | 3.0 | 72 |
| EP-1 | 3.4 | 75 |
| E-10 | 1.0 | 10 |
| E-7/Na | 0 | 0 |
| E-10/Na | 0 | 0 |
| E-11/Na | 0 | 0 |
| E-12/Na | 0 | 0 |

EXAMPLE 54

The emulsion E-7 was adjusted to a solid content of 5% by weight, and sulfonic acid groups of this emulsion were neutralized by adding sodium hydrogencarbonate to prepare an emulsion whose sulfonic acid groups were converted to sodium salts by 10 mol % (10Na), 50 mol % (50Na) or 100 mol % (100 Na). Then, the so-prepared emulsions were measured for adhesion strength by the same tensile test as that in Example 52. The emulsions showed a tendency that the adhesion strength decreased with an increase in the molar ratio of sodium sulfonate to sulfonic acid group, and the results were E-7 (8.2 MPa), 10Na (5.9 MPa), 50Na (3.0 MPa) and 100 Na (0 MPa). Table 6 shows the results.

TABLE 6

| Emulsion No. | SO$_3$H group (mol %) | Tensile adhesion strength |
|---|---|---|
| E-7 (ONa) | 100 | 8.2 |
| 10 Na | 90 | 5.9 |
| 50 Na | 50 | 3.0 |
| 100 Na | 0 | 0.0 |

COMPARATIVE EXAMPLE 15

A commercially available preparation for preventing cervical hyperesthesia (VARNAL, supplied by CETYLITE INDUSTRIES INC., U.S.A.) was tested for dental tubules sealability in the same manner as in Example 53 to show that only 40% of the tubules were sealed.

What is claimed is:

1. An emulsion of a water insoluble polymer, in which the polymer consists essentially of
   (a) a recurring unit derived from a (meth)acrylate,
   (b) a recurring unit derived from a vinyl compound having a group of —SO$_3$R in which R is a hydrogen atom, an alkali metal atom or ammonium ion and
   (c) a recurring unit derived from a vinyl compound containing a group of —COOR$_4$ in which R$_4$ is a hydrogen atom, an alkali metal atom or ammonium ion, or a group of —OPO(OR$_5$)$_2$ in which R$_5$ is a hydrogen atom, an alkali metal atom or ammonium ion, and
   is derived from a mixture of the (a) (meth)acrylate, (b) the vinyl compound having the group of —SO$_3$R and (c) the vinyl compound containing the group of —COOR$_4$ or the group of —OPO(OR$_5$)$_2$ in the molar ratio of (meth)acrylate:total of the two vinyl compounds of 99:1 to 50:50 and in the molar ratio of the vinyl compound having the group of —SO$_3$R to the vinyl compound containing the group of —COOR$_4$ or the group of —OPO(OR$_5$)$_2$ of 99:1 to 1:99 by a soap-free emulsion polymerization, and wherein at least 50 mol % of the vinyl compound having the group of —SO$_3$R is a vinyl compound having the group —SO$_3$H.

2. An emulsion of a water insoluble polymer obtained by emulsion-polymerizing (meth)acrylate in the presence of an emulsion consisting essentially of the polymer recited in claim 1 as an emulsifying agent.

3. An adhesive composition consisting essentially of the emulsion of the polymer recited in claim 1.

4. An adhesive composition consisting essentially of the emulsion of the water insoluble polymer recited in claim 2.

5. A dental adhesive composition consisting essentially of the emulsion of the water insoluble polymer recited in claim 1.

6. A dental adhesive composition consisting essentially of the emulsion of the water insoluble polymer recited in claim 2.

7. An adhesive composition consisting essentially of the emulsion of a water insoluble polymer consisting essentially of a polymer obtained by emulsion-polymerizing (meth)acrylate in the presence of the emulsion of a water insoluable polymer as an emulsifying agent, said polymer of the latter emulsion as the emulsifying agent consisting essentially of a polymer obtained by emulsion-polymerizing (a) a (meth) acrylate and (b1) a vinyl compound having a group of —SO$_3$R in which R is hydrogen atom in the absence of a soap in an (a):(b1) molar ratio of 99:1 to 50:50.

8. An adhesive composition consisting essentially of the emulsion of a water insoluble polymer consisting essentially of a polymer obtained by emulsion-polymerizing (meth)acrylate in the presence of the emulsion of a water insoluble polymer as an emulsifying agent, said polymer of the latter emulsion as the emulsifying agent consisting essentially of a polymer obtained by emulsion-polymerizing (a) a (meth) acrylate and (b1) a vinyl compound having a group of —SO$_3$R in which R is an alkali metal atom or ammonium ion in the absence of a soap in an (a):(b1) molar ratio of 99:1 to 50:50, and thereafter converting said group of —SO$_3$R to —SO$_3$H group.

9. An adhesive composition consisting essentially of emulsion of a water insoluble polymer consisting essentially of a polymer obtained by emulsion-polymerizing (meth)acrylate in the presence of a water insoluble polymer as an emulsifying agent, said polymer of the latter emulsion as the emulsifying agent consisting essentially of a polymer obtained by emulsion-polymerizing (a) a (meth) acrylate and (b1) a vinyl compound having a group of —SO$_3$R in which R is a hydrogen atom and (c1) a vinyl compound containing a group of —COOR$_4$ in which R$_4$ is a hydrogen atom or a group of —OPO(OR$_5$)$_2$ in which R$_5$ is a hydrogen atom, in the absence of a soap in the molar ratio of (meth) acrylate (a): total of the two vinyl compounds (b1) and (c1) of 99:1 to 50:50 and the molar ratio of the vinyl compound (b1):the vinyl compound (c1) of 99:1 to 1:99.

10. An adhesive composition consisting essentially of the emulsion of a water insoluble polymer consisting essentially of a polymer obtained by emulsion-polymerizing (meth)acrylate in the presence of the emulsion of a water insoluble polymer as an emulsifying agent, said polymer of the latter emulsion as the emulsifying agent consisting essentially of a polymer obtained by emulsion-polymerizing (a) a (meth-)acrylate, (b1) a vinyl compound having a group of —SO$_3$R in which R is an alkali metal ion or ammonium ion and (c1) a vinyl compound containing a group of —COOR$_4$ in which R4 is an alkali metal atom or ammonium ion, or a group of —OPO(OR$_5$)$_2$ in which R$_5$ is an alkali metal atom or ammonium ion, in the absence of a soap in the molar ratio of (meth)acrylate (a):total of the two vinyl compounds (b1) and (c1) of 99:1 to 50:50 and in the molar ratio of the vinyl compound (b1): the vinyl compound (c1) of 99:1 to 1:99, and thereafter converting said groups of —SO$_3$R, —COOR$_4$ and —OPO(OR$_5$)2 to —SO$_3$H, —COOH and OPO(OH)$_2$, respectively.

11. A dental adhesive composition consisting essentially of the emulsion of a water insoluble polymer consisting essentially of a polymer obtained by emulsion-polymerizing (meth)acrylate in the presence of the emulsion of a water insoluable polymer as an emulsifying agent, said polymer of the latter emulsion as the emulsifying agent consisting essentially of a polymer obtained by emulsion-polymerizing (a) a (meth)acrylate and (b1) a vinyl compound having a group of —SO$_3$R in which R is hydrogen atom in the absence of a soap in an (a):(b1) molar ratio of 99:1 to 50:50.

12. A dental adhesive composition consisting essentially of emulsion of emulsion of a water insoluble polymer consisting essentially of a polymer obtained by emulsion-polymerizing (meth) acrylate in the presence of the emulsion of a water insoluble polymer as an emulsifying agent, said polymer of the latter emulsion as the emulsifying agent consisting essentially of a polymer obtained by emulsion-polymerizing (a) a (meth) acrylate and (b1) a vinyl compound having a group of —SO$_3$R in which R is an alkali metal atom or ammonium ion in the absence of a soap in an (a):(b1) molar ratio of 99:1 to 50:50, and thereafter converting said group of —SO$_3$R to —SO$_3$H group.

13. A dental adhesive composition consisting essentially of the emulsion of a water insoluble polymer consisting essentially of a polymer obtained by emulsion-polymerizing (meth)acrylate in the presence of a water insoluble polymer as an emulsifying agent, said polymer of the latter emulsion as the emulsifying agent consisting essentially of a polymer obtained by emulsion-polymerizing (a) a (meth) acrylate and (b1) a vinyl compound having a group of —$SO_3R$ in which R is a hydrogen atom and (c1) a vinyl compound containing a group of —$COOR_4$ in which $R_4$ is a hydrogen atom or a group of —$OPO(OR_5)_2$ in which $R_5$ is a hydrogen atom, in the absence of a soap in the molar ratio of (meth) acrylate (a): total of the two vinyl compounds (b1) and (c1) of 99:1 to 50:50 and the molar ratio of the vinyl compound (b1):the vinyl compound (c1) of 99:1 to 1:99.

14. A dental adhesive composition consisting essentially of the emulsion of a water insoluble polymer consisting essentially of a polymer obtained by emulsion-polymerizing (meth)acrylate in the presence of the emulsion of a water insoluble polymer as an emulsifying agent, said polymer of the latter emulsion as the emulsifying agent consisting essentially of a polymer obtained by emulsion-polymerizing (a) a (meth)acrylate, (b1) a vinyl compound having a group of —$SO_3R$ in which R is an alkali metal atom or ammonium ion and (c1) a vinyl compound containing a group of —$COOR_4$ in which R4 is an alkali metal atom or ammonium ion, or a group of —$OPO(OR_5)_2$ in which $R_5$ is an alkali metal atom or ammonium ion, in the absence of a soap in the molar ratio of (meth) acrylate (a):total of the two vinyl compounds (b1) and (c1) of 99:1 to 50:50 an in the molar ratio of the vinyl compound (b1): the vinyl compound (c1) of 99:1 to 1:99, and thereafter converting said groups of —$SO_3R$, —$COOR_4$ and —$OPO(OR_5)_2$ to —$SO_3H$, —COOH and $OPO(OH)_2$, respectively.

15. A dental adhesive primer composition consisting essentially of the emulsion of a water insoluble polymer consisting essentially of a polymer obtained by emulsion-polymerizing (meth)acrylate in the presence of the emulsion of a water insoluable polymer as an emulsifying agent, said polymer of the latter emulsion as the emulsifying agent consisting essentially of a polymer obtained by emulsion-polymerizing (a) a (meth) acrylate and (b1) a vinyl compound having a group of —$SO_3R$ in which R is hydrogen atom in the absence of a soap in an (a):(b1) molar ratio of 99:1 to 50:50.

16. A dental adhesive primer composition consisting essentially of the emulsion of a water insoluble polymer consisting essentially of a polymer obtained by emulsion-polymerizing (meth) acrylate in the presence of the emulsion of a water insoluable polymer as an emulsifying agent, said polymer of the latter emulsion as the emulsifying agent consisting essentially of a polymer obtained by emulsion-polymerizing (a) a (meth) acrylate and (b1) a vinyl compound having a group of —$SO_3R$ in which R is an alkali metal atom or ammonium ion in the absence of a soap in an (a):(b1) molar ratio of 99:1 to 50:50, and thereafter converting said group of —$SO_3R$ to —$SO_3H$ group.

17. A dental adhesive primer composition consisting essentially of the emulsion of a water insoluble polymer consisting essentially of a polymer obtained by emulsion-polymerizing (meth)acrylate in the presence of a water insoluble polymer as an emulsifying agent, said polymer of the latter emulsion as the emulsifying agent consisting essentially of a polymer obtained by emulsion-polymerizing (a) a (meth) acrylate and (b1) a vinyl compound having a group of —$SO_3R$ in which R is a hydrogen atom and (c1) a vinyl compound containing a group of —$COOR_4$ in which $R_4$ is a hydrogen atom or a group of —$OPO(OR_5)_2$ in which $R_5$ is a hydrogen atom, in the absence of a soap in the molar ratio of (meth)acrylate (a) total of the two vinyl compounds (b1) and (c1) of 99:1 to 50:50 and the molar ratio of the vinyl compound (b1):the vinyl compound (c1) of 99:1 to 1:99.

* * * * *